US007995813B2

(12) United States Patent
Foshee et al.

(10) Patent No.: US 7,995,813 B2
(45) Date of Patent: Aug. 9, 2011

(54) REDUCING VARIATION IN RADIATION TREATMENT THERAPY PLANNING

(75) Inventors: Jacob Foshee, Houston, TX (US); Hui-Min Chao, Houston, TX (US)

(73) Assignee: Varian Medical Systems, Inc., Palo Alto, CA (US)

( * ) Notice: Subject to any disclaimer, the term of this patent is extended or adjusted under 35 U.S.C. 154(b) by 1153 days.

(21) Appl. No.: 11/734,718

(22) Filed: Apr. 12, 2007

(65) Prior Publication Data

US 2008/0253518 A1 Oct. 16, 2008

(51) Int. Cl.
*G06K 9/00* (2006.01)
(52) U.S. Cl. ........................................ 382/128
(58) Field of Classification Search .......... 382/128–134; 128/920–925; 356/39–49; 600/407–414, 600/424–426; 345/581–618
See application file for complete search history.

(56) References Cited

U.S. PATENT DOCUMENTS

| | | | | |
|---|---|---|---|---|
| 2005/0004443 A1* | 1/2005 | Okerlund et al. | ............. | 600/407 |
| 2005/0041843 A1* | 2/2005 | Sawyer | ......................... | 382/128 |
| 2005/0111621 A1* | 5/2005 | Riker et al. | ...................... | 378/65 |
| 2006/0171586 A1* | 8/2006 | Georgescu et al. | ........... | 382/173 |
| 2007/0041496 A1* | 2/2007 | Olivera et al. | .................. | 378/65 |
| 2007/0041499 A1* | 2/2007 | Lu et al. | .......................... | 378/65 |
| 2007/0167699 A1* | 7/2007 | Lathuiliere et al. | ........... | 600/407 |

\* cited by examiner

*Primary Examiner* — Samir A Ahmed
*Assistant Examiner* — Atiba O Fitzpatrick
(74) *Attorney, Agent, or Firm* — Lapus Greiner Lai Corsini, LLC; Theodore Lapus

(57) ABSTRACT

A method and apparatus are disclosed that reduces variation in radiation therapy treatment planning among plurality of users within the same or different geographic locations. The system includes a method and an apparatus that provide users with the knowledge information and utilizing the knowledge information to contour target volumes for radiation treatment planning. The mode of operation includes utilizing a stand-alone workstation or a server computer connected to the plurality of thin client workstations.

20 Claims, 6 Drawing Sheets

500 providing the users 200 with the knowledge information
502

Use the knowledge information to contour target volumes for radiation treatment planning
504

Fig. 6

REDUCING VARIATION IN RADIATION TREATMENT THERAPY PLANNING

BACKGROUND OF THE INVENTION

1. Field of the Invention

The present invention generally relates to a methods and system for radiation therapy treatment planning, more specifically to an improved method and system that reduces variations in the planning of radiation therapy treatment.

2. Description of the Related Art

Image-guided three-dimensional (3-D) radiotherapy aims at delivering the largest possible and the most homogeneous radiation dose to a tumor target while keeping the dose to surrounding normal tissues to a minimum. Thus, the prime step in radiotherapy planning is to determine and to delineate a target volume in three dimensions in order to produce a treatment volume which will encompass the tumor (and normal tissues) with as much precision as possible.

The routine use of 3-D treatment planning in curative radiation therapy and the growing implementation of intensity-modulated radiotherapy (IMRT) or proton treatment in many centers require a very accurate knowledge of the volumes to be treated, with a good reproducibility, not only within same physician at different period of time but also between physicians of varying geographic practices and locations. Older techniques used larger and unshaped fields, and this has led to either a limitation of the total dose with many treatment failures, or to an excessive rate of complications. Conversely, new technologies, such as IMRT or proton, if not associated with an extremely careful definition of the target, may lead to an excess of geographic misses and local failures. The International Commission on Radiation Units and Measurements (ICRU) Reports 50 and 62, published in 1993 and 1999, have provided a formal definition to describe volumes in radiation planning. In brief, the gross tumor volume (GTV) is the gross extent of the malignancy. The clinical target volume (CTV) is the GTV plus a margin to include local subclinical tumor spread. The CTV can also include regional nodes. The GTV and CTV are based on anatomic, biological and clinical considerations and do not account for the technical factors of treatment. The planning target volume (PTV) is the CTV plus a margin to ensure that the CTV receives the prescribed dose. Previous studies have shown that large discrepancies were found when different physicians were asked to delineate volumes in the same patient. These discrepancies are worrisome when considering the high precision achieved with conformal therapy and even more with IMRT. It has been stated that inadequate definition of the GTV/CTV leads to a systematic geographic miss of the tumor and that, for some locations, these inconsistencies may dominate all other errors in radiotherapy planning and delivery. A recent study revealed the following:

(1) variation in knowledge and/or interpretation in the basic ICRU definitions;
(2) variation in understanding and/or concept for microscopic tumor extent (CTV);
(3) variation between the theoretical knowledge (stated region of interest) and the practice (drawn region of interest).

Therefore, measures that are able to decrease discrepancies and improve inter-user discrepancy will have a significant clinical impact on the success of curing cancer.

SUMMARY OF THE INVENTION

A method is disclosed that provides a knowledge based reference library and computer apparatus (both software and hardware) to standardize 3-D radiation therapy planning among users (including physicians, medical physicists, medical dosimetrists . . . etc.) of varying geographic locations and training background. This method establishes a dynamic communication between a knowledge information repository which provides the updated medical information on target volume determination and delineation as well as optimized planning guidance for varying treatment planning systems to produce radiotherapy treatment plans. This system will enable a plurality of users within the same or among different medical practices or a plurality of users at different geographic locations to provide consistent medical services (radiation therapy) to cancer patients. Autocontouring methods disclosed in this invention can also reduce the amount of time that users need to spend to contour the tumor and normal tissue target volumes and generate an optimal treatment plan for cancer patients.

The present invention generally relates to a method for reducing variations in radiation therapy treatment planning among a plurality of users. The method comprises the steps of: (a) providing the users with knowledge information; (b) utilizing the knowledge information to contour target volumes for a radiation treatment planning.

BRIEF DESCRIPTION OF THE DRAWINGS

So that the manner in which the above recited features, advantages and objects of the present invention are attained and can be understood in detail, a more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENTS

Before describing in detail embodiments that are in accordance with the present invention, it should be observed that the embodiments reside primarily in combinations of method steps and apparatus components related to the selection of a set of target volume contours based on guidance from a disease-matched expert case. Accordingly, the apparatus components and method steps have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

In this document, relational terms such as first and second, top and bottom, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

It will be appreciated that embodiments of the invention described herein may be comprised of one or more conventional processors and unique stored program instructions that control the one or more processors to implement, in conjunction with certain non-processor circuits, some, most, or all of the functions of a method relating to the selection of a set of target volume contours based on guidance from a disease-matched expert case described herein. The non-processor circuits may include, but are not limited to, a radio receiver, a radio transmitter, signal drivers, clock circuits, power source circuits, and user input devices. As such, these functions may be interpreted as steps of a method to perform functions relating to the selection of a set of target volume contours based on guidance from a disease-matched expert case. Alternatively, some or all functions could be implemented by a state machine that has no stored program instructions, or in one or more application specific integrated circuits (ASICs), in which each function or some combinations of certain of the functions are implemented as custom logic. Of course, a combination of the two approaches could be used. Thus, methods and means for these functions have been described herein. Further, it is expected that one of ordinary skill, notwithstanding possibly significant effort and many design choices motivated by, for example, available time, current technology, and economic considerations, when guided by the concepts and principles disclosed herein will be readily capable of generating such software instructions and programs and ICs with minimal experimentation.

Figure 1:
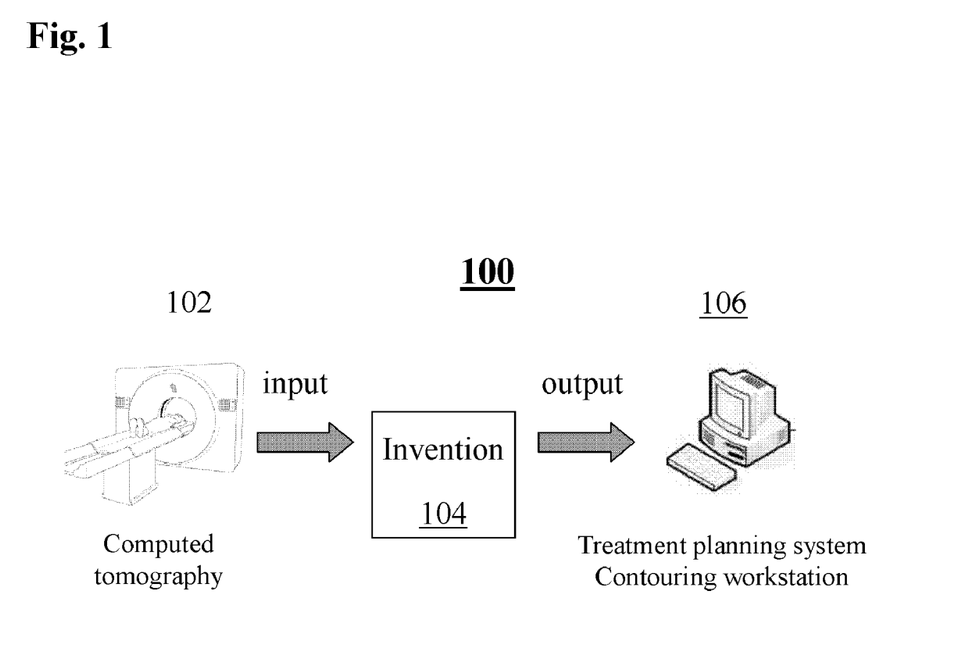
FIG. 1 is an exemplified depiction incorporating the present invention.

Referring to FIGS. 1-6, a set of depictions of the present invention is shown. In FIG. 1, an exemplified depiction 100 incorporating the present invention is shown. A patient, medical data acquiring device 102 such as a computed tomography simulator inputs a set of acquired patient, medical data into a device or system 104 of the present invention. A finalized result of system 104 is output and used by a treatment planning system contouring workstation 106.

Figure 2:
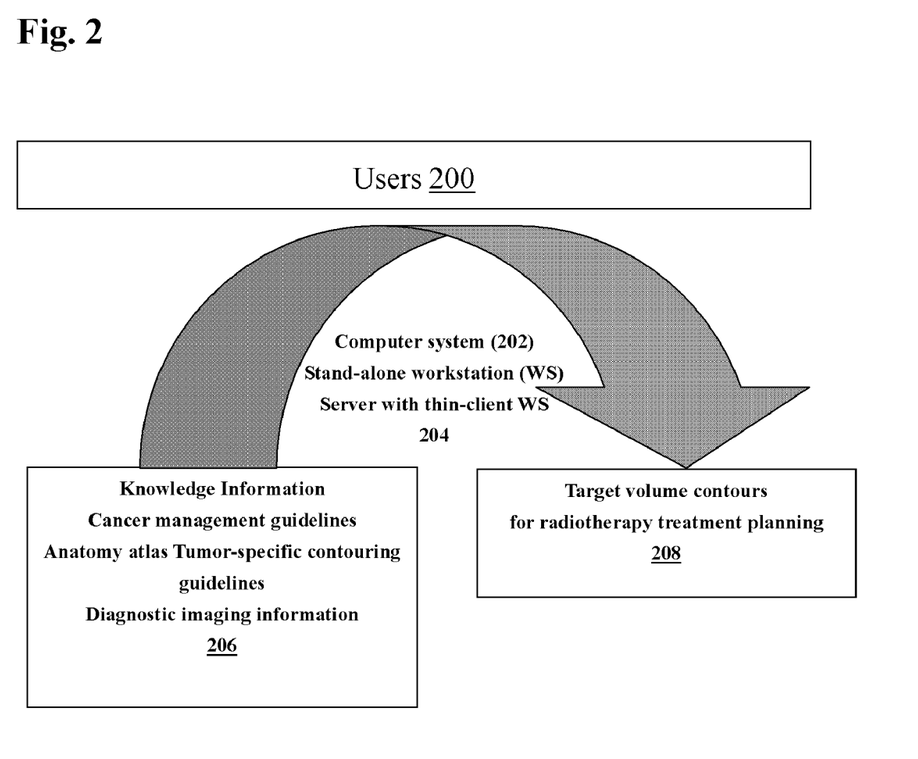
FIG. 2 is an example of various elements in accordance with some embodiments of the invention.

In FIG. 2, various elements associated with system 104 of the present invention is shown. A plurality of users 200 is associated with system 104 both physically close together or remote to each other. The users 200 comprise physicians, medical physicists, medical dosimetrists, physician assistants, and radiation therapy technicians. Users 200 have access to a computer system 202 via a sub-system 204 comprising a stand-alone workstation, or a server with thin-client workstation, or any suitable device incorporating the present invention. Computer system 202 further comprises a knowledge information sub-system 206 including data retrieving and storing capabilities. Knowledge information sub-system 206 is informationally coupled to 204. Knowledge information sub-system 206 comprises such stored and retrievable information as cancer management guidelines, anatomy atlas, tumor-specific contouring guidelines, and diagnostic imaging information. Computer system 202 still further comprises multi-user 200 processed information 208 such as target volume contours for radiotherapy treatment planning. Multi-user 200 is defined as at least two users 200, with at least one user 200 who is predetermined by computer system 202 to be an expert in processing information 208.

Figure 3:
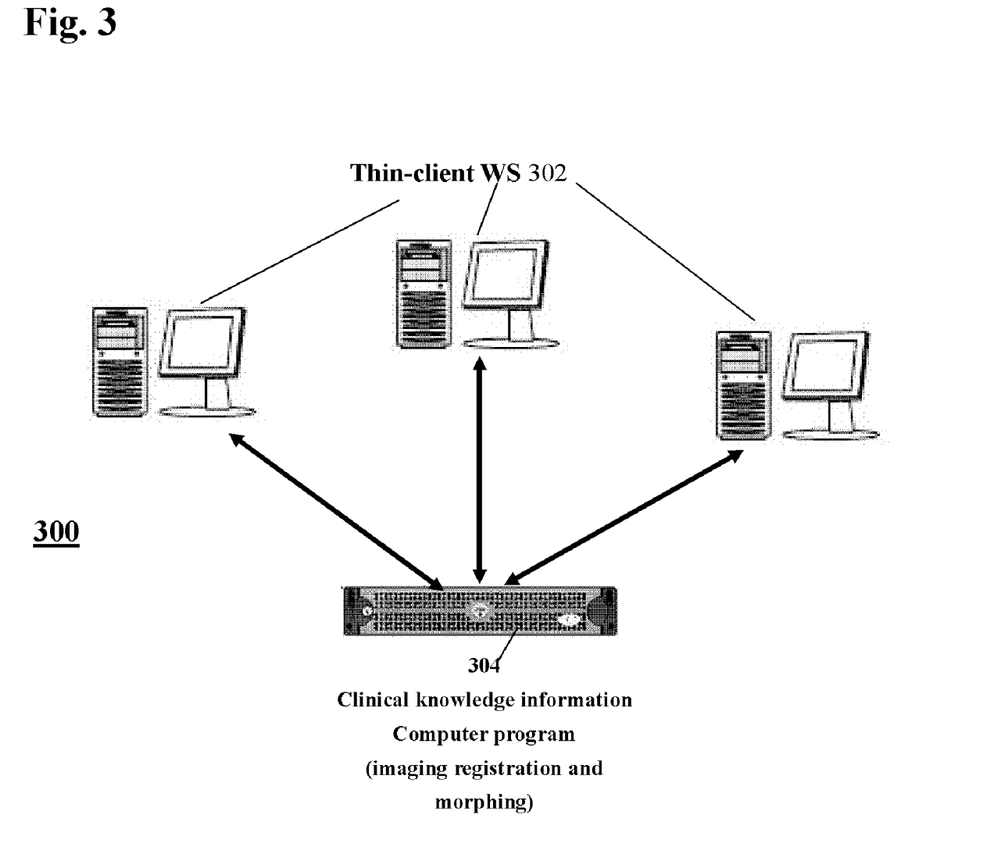
FIG. 3 is an example of a computer network in accordance with some embodiments of the invention.

In FIG. 3, a computer network 300 for an embodiment of the present invention is shown. A plurality of workstations 302 such as thin client work stations, wherein each workstation 302 is adapted to be used by users 200. The set of workstations 302 is coupled to a server 304, wherein clinical knowledge information, computer programs for such things as imaging registration and morphing are stored or run. It should be noted that other devices such as laptops with wireless capabilities, personal digital assistants (PDAs), or any suitable terminal may be used by users 200 instead of workstations 302.

Figure 4:
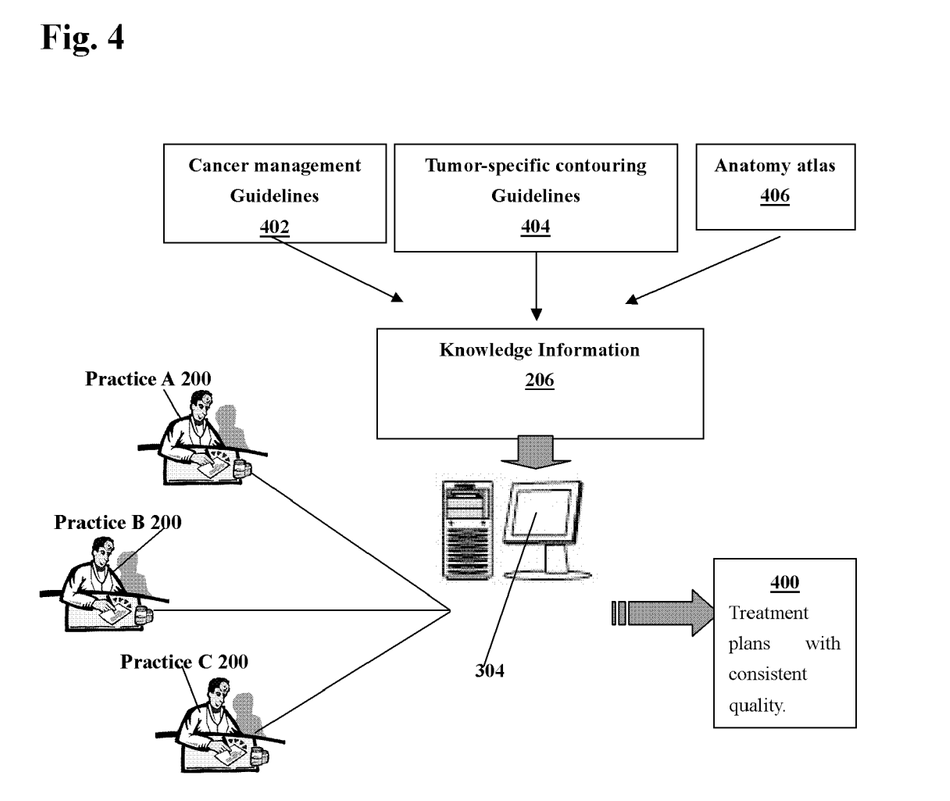
FIG. 4 is an example a different perspective in accordance with some embodiments of the invention.

In FIG. 4, a different perspective of the present invention is shown. Similar to FIG. 2, knowledge information sub-system 206 comprises cancer management guidelines 402, anatomy atlas 406, tumor-specific contouring guidelines 404, and diagnostic imaging information. Users 200 respectively positioned at different doctors' offices are informationally coupled to server 304 for the access or use of the above mentioned information including cancer management guidelines 402, anatomy atlas 406, tumor-specific contouring guidelines 404, and diagnostic imaging information. In other words, knowledge information sub-system 206 is informationally coupled to server 304. With the collaborations of users 200 and access to knowledge information sub-system 206, treatment plans 400 with consistent quality are achieved. This way, contouring time is significantly reduced, especially for less experienced physicians as some users 200 who are not used to contouring.

Figure 5:
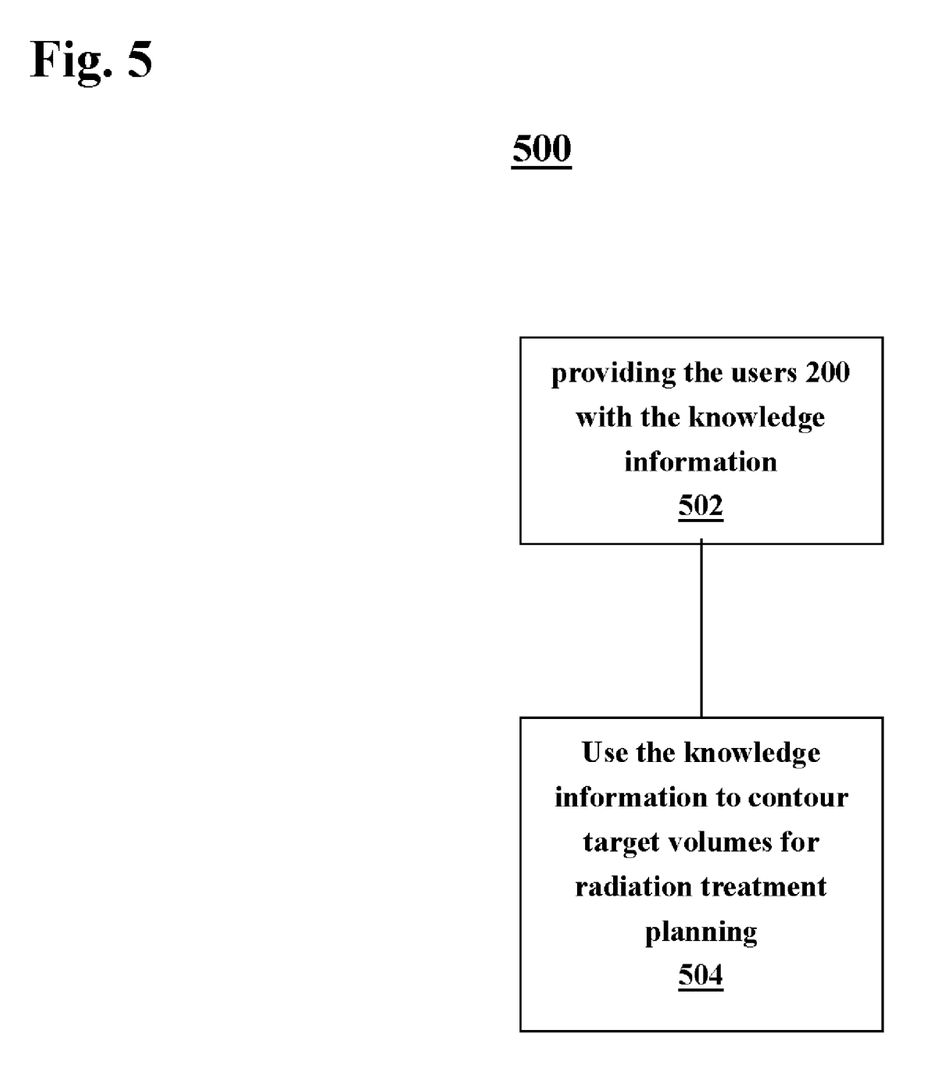
FIG. 5 is an example of a method in accordance with some embodiments of the invention.

Referring to FIG. 5, a flowchart 500 depicting a method for reducing variation in radiation therapy treatment planning among a plurality of users 200 is shown. The method comprises the steps of: (a) providing the users 200 with the knowledge information (Step 502). The users 200 comprise but are not limited to physicians, medical physicists, medical dosimetrists, physician assistants, and radiation therapy technicians. The knowledge information is used to contour target volumes for radiation treatment planning (Step 504). The knowledge information 206 comprises cancer management guidelines derived from consensus among plurality of physicians within one practice group. The consensus may be among plurality of thought leaders in a specific cancer treatment. Alternatively, the consensus may be among a plurality of cancer centers.

The knowledge information 206 comprises an atlas that depicts a plurality of cross section anatomical images and provides information on the names and functions of specific tissues or organs. Furthermore, the knowledge information 206 comprises tumor (cancer) specific target volume contours that are derived from a consensus among plurality of physicians within one practice group. Alternatively, the consensus may be among thought leaders on specific cancer management and radiation treatment planning regions of interest as depicted on functional images such as PET, SPECT, MRI, dynamic MRI, MR spectroscopy, ultrasound, or dynamic CT. Tumor-specific target volumes are categorized by tumor location, size, staging, gender, and laterality (right or left sided, or centrally located). The knowledge information 206 is constantly updated.

The contouring target volumes for radiation treatment planning may performed manually by the users 200 utilizing contouring tools on a contouring workstation or treatment planning computer with the knowledge information 206 serving as the guidance Alternatively the contouring target volume for radiation treatment planning is performed automatically using an autocontouring computer program. The autocontouring computer program comprises plurality of tumor-specific target volume contours on tumor-specific CT images. The autocontouring computer program comprises a computer programs that overlays a plurality of tumor-specific target volume contours onto patient's CT images.

The autocontouring computer program comprises a computer program that morphs a plurality of tumor-specific target volume contours to fit patient's anatomy on a plurality of CT images. The autocontouring computer program comprises contour modification tools that allow users 200 to modify the morphed target volume contours on a patient's CT images. The contouring target volumes for radiation treatment planning is performed by using the tumor-specific target volume contours on reference CT images as the guidance when users 200 modify patient's target volume contours.

Figure 6:
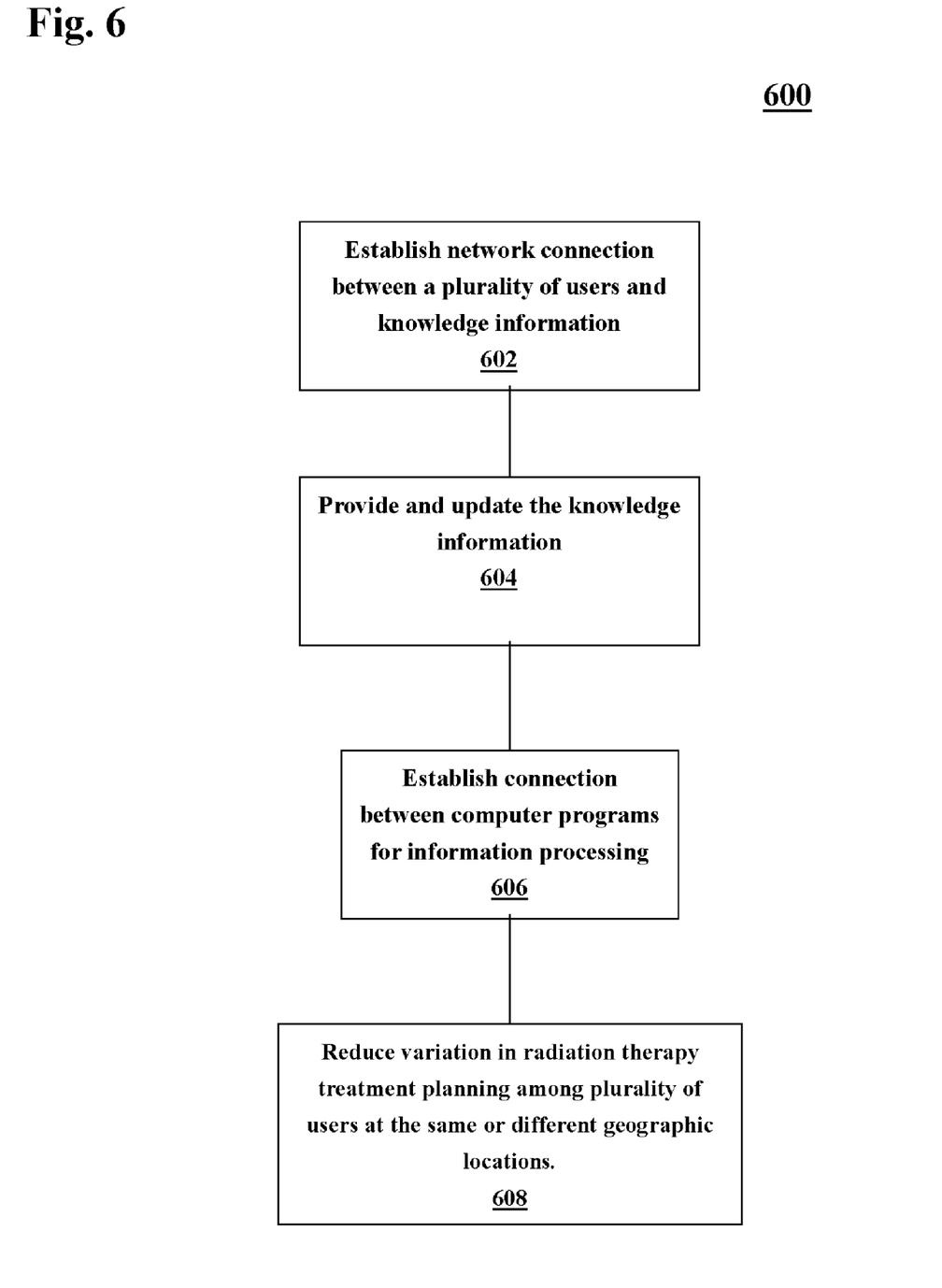
FIG. 6 is an example of a flowchart in accordance with some embodiments of the invention.

Referring to FIG. 6, a flowchart 600 of the present invention is shown. An apparatus for reducing variation in radiation therapy treatment planning among plurality of users 200 is provided. A network connection between the plurality of users 200 and knowledge information 206 is established (Step 602). The knowledge information 206 as is updated (Step 604). A connection between computer programs that register and morph knowledge information (contours) to the patient's computed tomography is established. (Setp 606) Users 200 comprise physicians, medical physicists, medical dosimetrists, physician assistants, and radiation therapy technicians. The establishing of the network connection between the plurality of users 200 and knowledge information 206 comprising a stand-alone computer workstation with connection through a local network provides access for input and output. The present invention is able to reduce variation in radiation treatment planning and improve the quality among users 200 of different education and training backgrounds (Step 608).

The network connection between the plurality of users 200 and knowledge information 206 consist of a server computer connected to the network to provide access for input and output and for serving a plurality of thin client workstations. The thin client workstation is a computer in a client-server architecture network which depends primarily on the central server for processing activities. The input of may be a CT imaging data set from a CT simulator. The output may be a treatment planning system or a contouring workstation.

The knowledge information 206 is updated by periodically download from a source through Internet or manually by the users 200 using CD or DVD disc or other similar method. The network connection among the plurality of users 200 of the same or different geographic locations is a secured local network such as a virtual private network (VPN) through which traffic can be carried over a public networking infrastructure (e.g. the Internet) on top of standard protocols, or over a service provider's private network with a defined Service Level Agreement (SLA) between the VPN customer and the VPN service provider.

In the foregoing specification, specific embodiments of the present invention have been described. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

What is claimed is:

1. A method for reducing variation in radiation therapy treatment planning among a plurality of users, comprising the steps of:
providing a system which contains a knowledge information; providing a workstation which is configured to provide the users with the knowledge information received from the system; providing a processor which is configured to use the knowledge information to contour target volumes for a radiation treatment planning; whereby the target volumes will be contoured by the users according to the knowledge information as references such that two or more of the users provide consistent treatment planning.

2. The method of claim 1, wherein the users comprises physicians, medical physicists, medical dosimetrists, physician assistants, or radiation therapy technicians.

3. The method of claim 1, wherein the knowledge information comprises cancer management guidelines derived from a consensus among a plurality of physicians within one practice group.

4. The method of claim 1, wherein the knowledge information comprises consensus among a plurality of thought leaders in a specific cancer treatment group.

5. The method of claim 1, wherein the knowledge information comprises consensus among a plurality of cancer centers.

6. The method of claim 1, wherein the knowledge information comprises at least one atlas, wherein a plurality of cross sectional anatomical images is depicted.

7. The method of claim 1, wherein the knowledge information provides information on the names and functions of specific tissues or organs.

8. The method of claim 1, wherein the knowledge information comprises tumor (cancer) specific target volume contours being derived from consensus among plurality of physicians within one practice group.

9. The method of claim 1, wherein the knowledge information comprises tumor (cancer) specific target volume contours being derived from consensus among thought leaders on specific cancer management and radiation treatment planning.

10. The method of claim 1, wherein the knowledge information comprises tumor (cancer) specific target volume contours being derived from regions of interest as depicted on functional images such as PET, SPECT, MRI, dynamic MRI, MR spectroscopy, ultrasound, or dynamic CT.

11. The method of claim 1, wherein the knowledge information comprises tumor (cancer) specific target volume contours being derived from tumor-specific target volumes that are categorized by tumor location, size, staging, gender, and laterality (right or left sided, or centrally located).

12. The method of claim 1 further comprising continuously updating said knowledge information.

13. The method of claim 1, wherein said contouring target volumes for radiation treatment planning is performed manually by the users utilizing contouring tools on a contouring workstation or a treatment planning computer with said knowledge information serving as a guidance.

14. The method of claim 1, wherein said contouring target volumes for radiation treatment planning is performed automatically using an autocontouring computer program.

15. The method of claim 14, wherein said autocontouring computer program includes plurality of tumor-specific target volume contours on tumor-specific CT images.

16. The method of claim 14, wherein said autocontouring computer program includes a computer programs that overlays plurality of tumor-specific target volume contours onto patient's CT images.

17. The method of claim 14, wherein said autocontouring computer program includes a computer program that morphs plurality of tumor-specific target volume contours to fit patient's anatomy on plurality of CT images.

18. The method of claim 14, wherein said autocontouring computer program includes contour modification tools that allows users to modify a morphed target volume contours on patient's CT images.

19. The method of claim 1, wherein said contouring target volumes for radiation treatment planning is performed by using a tumor-specific target volume contours on reference CT images as a guidance when users modify patient's target volume contours.

20. A method for reducing variation in radiation therapy treatment planning among a plurality of users, comprising the steps of:
- providing the users with knowledge information;
- providing a processor which is configured to use the knowledge information to contour target volumes for a radiation treatment planning; and
- wherein the knowledge information comprises tumor (cancer) specific target volume contours being derived from tumor-specific target volumes that are categorized by tumor location, size, staging, gender, and laterality (right or left sided, or centrally located).

* * * * *